(12) United States Patent
Rathinasamy (10) Patent No.: US 8,470,740 B2
(45) Date of Patent: Jun. 25, 2013

(54) FLOWERING STIMULANT COMPOSITION USING NITROBENZENE

(75) Inventor: Theenachandran Rathinasamy, Madurai (IN)

(73) Assignee: Devi Crop Science Private Limited, Madurai (IN)

( * ) Notice: Subject to any disclaimer, the term of this patent is extended or adjusted under 35 U.S.C. 154(b) by 2145 days.

(21) Appl. No.: 10/961,493

(22) Filed: Oct. 8, 2004

(65) Prior Publication Data

US 2005/0266997 A1 Dec. 1, 2005

(30) Foreign Application Priority Data

Apr. 10, 2002 (IN) .............................. 263/MAS/2002
Jun. 24, 2002 (IN) .............................. 480/MAS/2002

(51) Int. Cl.
*A01N 33/06* (2006.01)
*A01N 33/18* (2006.01)
*A01N 25/30* (2006.01)

(52) U.S. Cl.
USPC ............................ 504/355; 504/362; 504/363

(58) Field of Classification Search
USPC .......................................... 504/355, 362, 363
See application file for complete search history.

(56) References Cited

U.S. PATENT DOCUMENTS 3,931,224 A * 1/1976 Santa et al. .................. 548/476
4,029,688 A * 6/1977 D'Silva .............................. 558/3
4,199,326 A * 4/1980 Fung ................................ 44/301
4,579,860 A * 4/1986 Tomita et al. ................. 514/380
5,004,846 A * 4/1991 Sato et al. ..................... 568/940
5,962,388 A * 10/1999 Sherry et al. .................. 510/238

FOREIGN PATENT DOCUMENTS

WO WO 03/086049 * 10/2003

OTHER PUBLICATIONS

Dugal, M., "Nitrobenzene and Nitrotoluenes," in: Kirk-Othmer Encyclopedia of Chemical Technology, ohn Wiley & Sons, Inc. (2005), vol. 17, pp. 1-6.*
HCAPLUS abstract 2002:607118 (2002).*
HCAPLUS abstract 1998:188806 (1998).*
Aziz et al., "Effect of "Flora" on the Growth and Yield of Wetland Rice," *J. Agric. Rural Dev.*, 7(1&2):9-13, 2009.

* cited by examiner

*Primary Examiner* — John Pak
(74) *Attorney, Agent, or Firm* — K&L Gates LLP (57) ABSTRACT

A flowering stimulant composition with Nitrobenzene for Agricultural and Horticultural flowering crops including Nitrobenzene as an Active ingredient, with Natural/Synthetic/Ionic (or) Non Ionic chemical surfactant and base with petro (or) Non petro solvent base. A typical example of 100 kg of the composition has 5 to 10 kgs. of Linear alkyl Benzene (Acid slurry), 1 to 2 kgs. of Sodium Hydroxide, 2 to 4 kgs. of Urea, 20 kg of Nitro Benzene and Quantum sufficientum Filler & stabilizer. In the case of 100 kgs. of granular formulation, the composition has 75 kg or 80 kg of Roasted or unroasted Bentonite clay or silica quartz sand granules, 10 kg or 15 kg Nitrobenzene and Quantum sufficientum Coating agent and De-activating Chemicals.

9 Claims, 8 Drawing Sheets

FIGURE 8

FLOWERING STIMULANT COMPOSITION USING NITROBENZENE

CROSS-REFERENCE TO RELATED APPLICATIONS

This application is a continuation of International Application No. PCT/IN2003/000138, filed on Apr. 3, 2003, which claims priority to and the benefit of Indian Patent Application No. 263/MAS/2002, filed on Apr. 10, 2002 and Indian Patent Application No. 480/MAS/2002, filed on Jun. 24, 2002.

FIELD OF INVENTION

This invention basically relates to the field of agricultural technology. Particularly, this invention is concerned with agricultural and horticultural crops. More particularly this invention relates to a flowering stimulant formulation and a process for the manufacture of said formulation which is meant for agricultural and horticultural crops. Salient feature of the invention is in identifying the flowering stimulant property as one of the essential properties of Nitrobenzene and inventing a novel composition containing nitrobenzene for application to agricultural and horticultural crops.

At the outset, it is to be understood that ensuring description only illustrates a particular form of this invention. However, such particular form is only an exemplary embodiment, without intending to imply any limitation on the scope of this invention. Accordingly, the description is to be understood as an exemplary embodiment and reading of the invention is not intended to be taken respectively.

The description outlines rather broadly preferred feature of the present invention so that those skilled in the art may better understand the detailed description of the invention that follows. Additional features of the invention will be described hereinafter that form the subject of claims of the invention. Those skilled in the art should appreciate that they can readily use the disclosed conception and specific embodiment as a basis for designing and modifying other structures for carrying on the same purposes of the present invention. Those skilled in the art should realize such equivalent conception do not depart from the spirit and scope of the invention in its broadest form.

BACKGROUND ART

Increasing the flowering of plants is of considerable importance in the field of Horticultural and Agricultural, since increased flowering means increased flower crop in Horticulture and increased flowering would result in increased fruiting, which again means a better crop in agriculture. There is no known prior art for increasing flowering in plants particularly. Hitherto the prior art was limited to using chemical and organic fertilizers in agriculture and horticulture which would result in overall increasing of the plant flowering quality and ultimately, yield. But there is a limitation to the use of the fertilizers and compost because of the law of diminishing returns. Fertilizers will increase vegetative growth also along with flowering and fruiting. Therefore flowering and fruiting do not take place to their peak levels.

It is the object of the present invention to formulate a composition, which would specifically stimulate higher flowering in plants and not merely result in over all growth of the plant.

A prior art search has been made world wide including at the U.S. Patent office, database and European Patent Office, database for prior art relating to flowering stimulants in plants. In view of the fact of the uniqueness of the invention, there has been no promising discoveries or inventions in the field. The applicant's invention has given substantial lead with confirmed results for various agriculture and horticulture crops.

SUMMARY OF INVENTION

The present invention addressees the problem of inventing and investigating a novel formulation which will stimulate flowering of agricultural and horticultural crops. This invention is a break through and an outcome of extensive research for finding out the basic raw material and formulation of the exact composition, Nitrobenzene tamed in a suitable formulation, used as spray or in granular form, which increases flower forming substances by altering auxin, cytokinin, gibbrellic acid and Ethylene ratio favourably tilting to a higher level of flower forming substances, thereby increasing flowers by more than 40 to 45% and yield thereby.

Preferred Embodiments

The inventor and the applicant have made great efforts to provide a novel and unique composition, which meets the requirement of agricultural and horticultural industries. Retaining common active principle, the present invention is envisaged in various formulations the details of which are as follows:

In an embodiment of invention, the present invention relates to a process of manufacturing flowering stimulant composition for Agricultural and Horticultural crops comprising Nitrobenzene as an Active ingredient with natural or synthetic surfactant and solvent base as carriers at the predetermined ratio for optimum results and with variable ratios as per requirements.

In another embodiment of invention, the present invention relates to a process of manufacturing a flowering stimulant composition with an optimum 20% Nitrobenzene in ionic surfactant base, with fillers enhancing the activity by synergism, wherein the process comprises of the ionic surfactant being manufactured by neutralizing the acid slurry and the resultant dark colour bleached to bring about honey colour to which nitrobenzene is charged and fillers added to secure the optimum 20% Nitrobenzene concentration.

In another embodiment of invention, the present invention relates to a process of manufacturing a flowering stimulant composition with Nitrobenzene, in non-ionic surfactant base, with fillers enhancing the activity by synergism, wherein the Nitrobenzene is at the optimum 20% concentration, which can be varied as per requirements.

In another embodiment of invention, the present invention relates to a process of manufacturing a flowering stimulant composition with the optimum 20% Nitrobenzene concentration by adding to a petro chemical solvent (Aromax, CIX, etc.), required quantity of Nitrobenzene and non ionic, ionic or cationic emulsifier or a mixture of all to get a flowering stimulant composition, wherein the Nitrobenzene is at the optimum 20% concentration which can be varied as per requirements.

In another embodiment of invention, the present invention relates to a process of manufacturing a flowering stimulant composition with 20% nitrobenzene in non petro chemical solvent (i.e. alcohol) by adding measured quantity of Nitrobenzene and thorough stirring with non ionic, ionic or cationic emulsifier or a mixture of all, to get flowering stimulant composition wherein the Nitrobenzene concentration is at an optimum 20% which can be varied as per requirements.

In another embodiment of invention, the present invention relates to a process of manufacturing flowering stimulant formulation for agricultural and horticultural crops wherein roasted or unroasted Bentonite clay or silica quarts sand granules with calcium silicate absorbent are used as a carrier to produce granules having Nitrobenzene at 10% or 15% strength or as per requirement.

In another embodiment of invention, the present invention relates to a process of manufacturing flowering stimulant formulation with 10% or 15% Nitrobenzene concentration W/W or as per requirement, in granule form wherein the process comprises of spraying the Nitrobenzene on Roasted or Unroasted Bentonite clay followed by spraying a coating agent after deactivating the Bentonite clay.

In another embodiment of invention, the present invention relates to a process of manufacturing flowering stimulant formulation with 10% or 15% Nitrobenzene concentration W/W or as per requirement, in granule form by spraying the Nitrobenzene on Silica Quartz Sand granule followed by spraying a suitable coating agent.

In another embodiment of invention, the present invention relates to a process of manufacturing flowering stimulant formulation by adding a premixed mixture of calcium silicate as the absorbent and china-clay as a bulk carrier to the main active ingredient Nitrobenzene, to which solid ironic surfactant like carboxylmethyl cellulose is added to obtain a composition having an optimum Nitrobenzene concentration of 20% or as per requirement.

In another embodiment of invention, this instant invention relates to a flowering stimulant composition having the following ingredients in the optimum proportion as stated herein for 100 kg:

| | |
|---|---|
| Linear alkyl Benzene (Acid Slurry) | 8 to 10 kg |
| Sodium Hydroxide | 1 kg to 2 kg |
| Nitrobenzene | 20 kg to 22 kg |
| Urea | 2 to 4 kg. |
| Filler & stabilizer | Quantum sufficientum |

In another embodiment of invention, the present invention relates to a flowering stimulant composition having the following ingredients in the optimum proportion as stated herein for 100 kg:

| | |
|---|---|
| Non ionic surfactant | 60 to 70 kg |
| Nitrobenzene | 20 kg to 22 kg |
| Filler & stabilizer | Quantum sufficientum (Q.S) |

In another embodiment of invention, the present invention relates to a flowering stimulant composition having the following ingredients in the optimum proportion as stated herein for 100 kg.

| | |
|---|---|
| Aromax or CIX or other Petrol chemical solvents. | 50 to 60 kg |
| Nitrobenzene | 20 kg to 22 kg |
| Non ionic, ionic or cationic emulsifier or mixed emulsifier. | 10 kg to 15 kg |
| Filler & Stabilizer | if needed. |

In another embodiment of invention, the present invention relates to a flowering stimulant composition having the following ingredients in the optimum proportion as stated herein for 100 kg.

| | |
|---|---|
| Non petro solvent (Alcohol) | 60 to 70 kg |
| Nitrobenzene | 20 kg to 22 kg |
| Non ionic or ionic or mixed emulsifier | 10 to 15 kg. |
| Filler & Stabilizer | if needed. |

In another embodiment of invention, the present invention relates to a flowering stimulant composition having the following ingredients in the optimum proportion as stated herein for 100 kg. Granule formulation with 10% or 15% Nitro Benzene by weight.

| | |
|---|---|
| Roasted Bentonite clay | 85 kg to 90 kg |
| Nitrobenzene | 10 kg or 15 kg |
| Deactivation chemicals | Q.S. |
| Coating agent | Q.S. |

In another embodiment of invention, the present invention relates to a flowering stimulant composition having the following ingredients in the optimum proportion as stated herein for 100 kg. Granule formulation with 10% or 15% Nitro Benzene by weight.

| | |
|---|---|
| Unroasted Bentonite clay | 85 kg to 90 kg |
| Nitrobenzene | 10 kg to 15 kg |
| Deactivation of chemicals | Q.S. |
| Coating agent | Q.S. |

In another embodiment of invention, the present invention relates to a flowering stimulant composition having the following ingredients in the optimum proportion as stated herein for 100 kg. Granule formulation with 10% or 15% Nitrobenzene by weight.

| | |
|---|---|
| Silica Quarts sand granules | 85 to 90 kg |
| Nitrobenzene | 10 or 15 kg. |
| Coating agent | Q.S. |

In another embodiment of invention, the present invention relates to a flowering stimulant composition having the following ingredients in the optimum proportion as stated herein for 100 kg. Granule formulation with 10% or 15% Nitrobenzene by weight.

| | |
|---|---|
| Nitro-Benzene | 20% |
| Ionic Solid Surfactant | 15% |
| Calcium Silicate | 10% |
| China Clay | Q.S.. |

Objects of Invention

Accordingly it is the primary object of the present invention to invent a novel flowering stimulant formulation which is unique.

It is another object of the present invention to invent a process for manufacturing a flowering stimulant formulation.

It is another object of the present invention to invent a novel composition which is a cost effective formulation.

Further objects of the invention will be clear from the following description.

BRIEF DESCRIPTION OF DRAWINGS

Now the invention will be described in detail in this complete specification with flow charts accompany the description. The flowcharts are given by way of non-limitative example intended to explain the invention.

DETAILED DESCRIPTION OF PREFERRED EMBODIMENT OF THIS INVENTION

Figure 1:
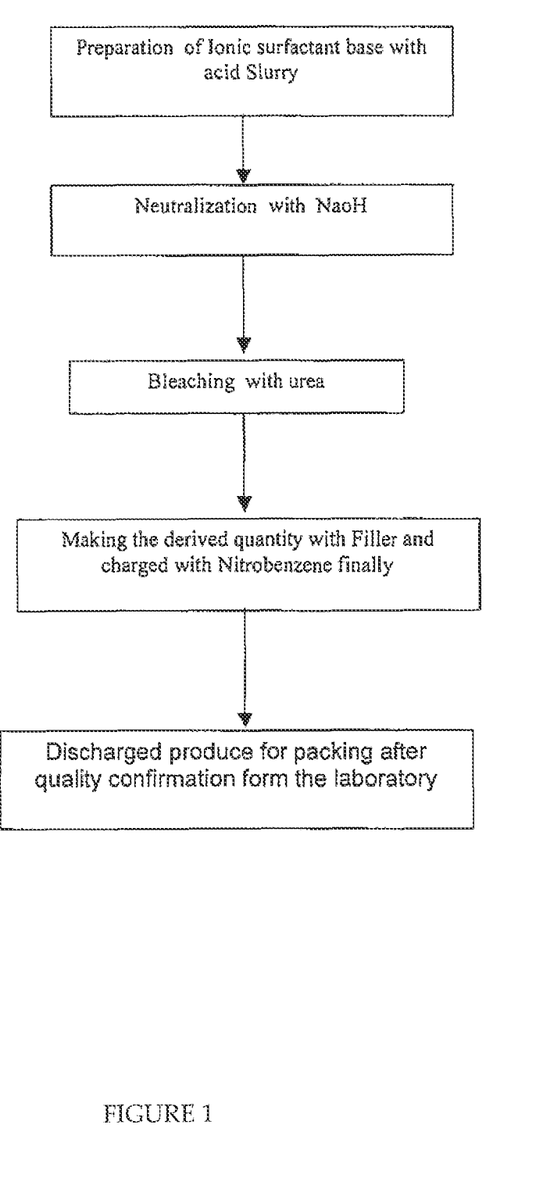
FIG. 1 shows the process detail of unique exo and endo thermic Process of the flowering stimulant composition, Boom Flower-n.
Figure 2:
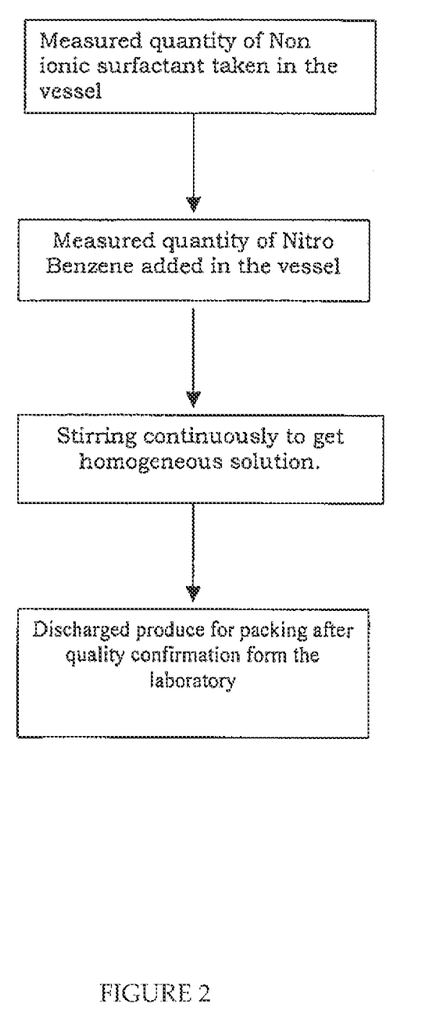
FIG. 2 shows processing details with non-ionic surfactant.
Figure 3:
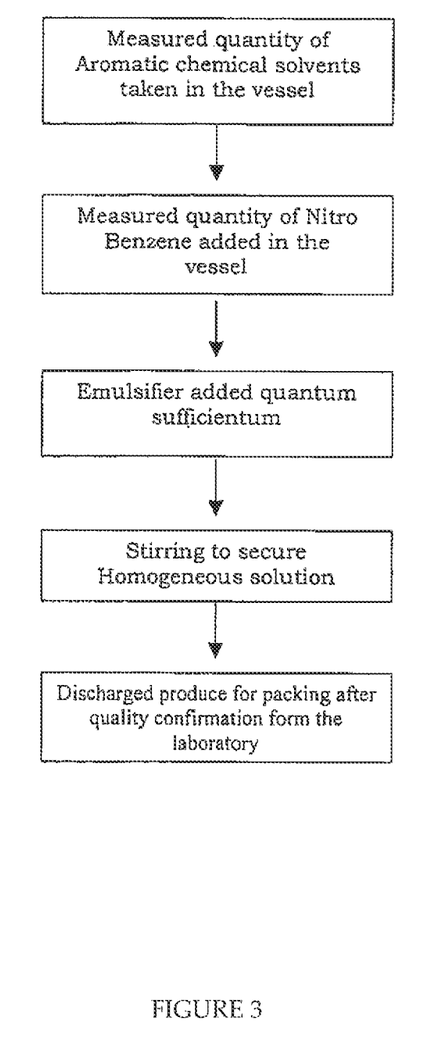
FIG. 3 shows processing details with aromatic petrochemical solvents.
Figure 4:
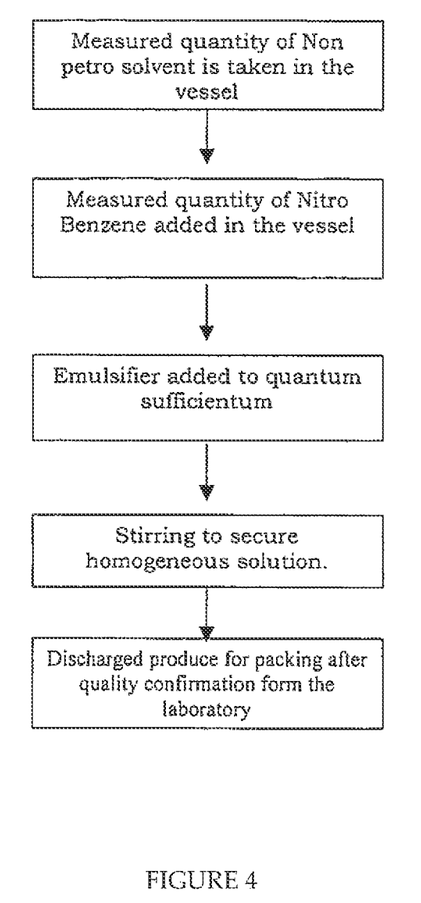
FIG. 4 shows processing details with non petro-solvents.
Figure 5:
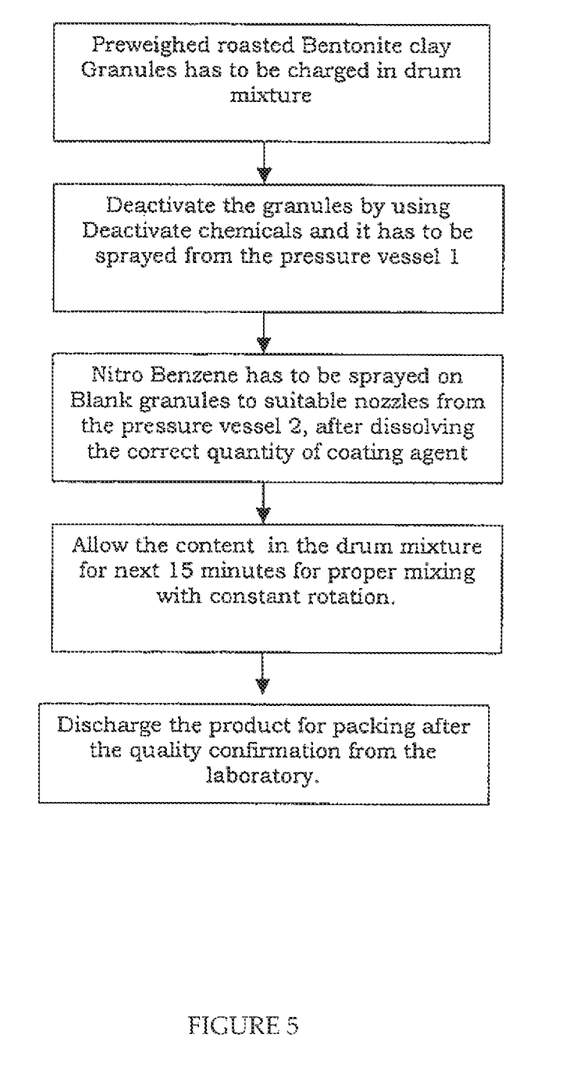
FIG. 5 shows processing details with Boom flower-n 10% & 15% Granules formulation with roasted Bentonite clay.
Figure 6:
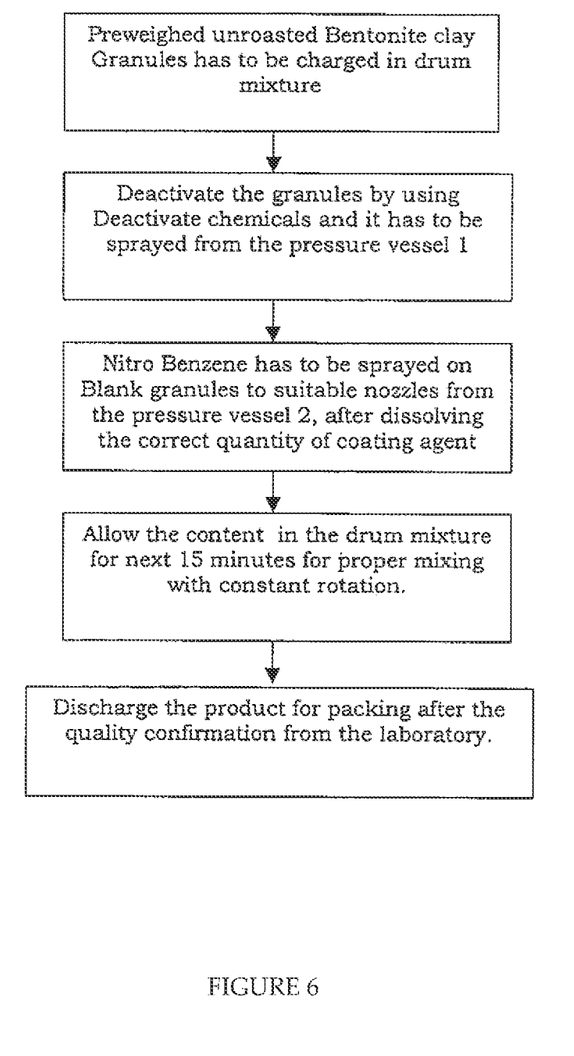
FIG. 6 shows process details for Boom Flower-n 10% to 15% granular formulation with un-roasted clay.
Figure 7:
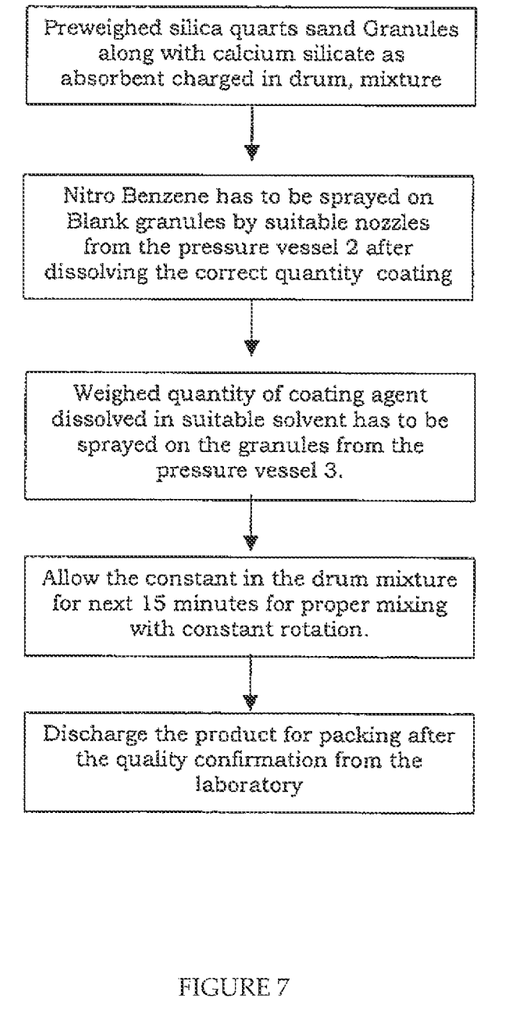
FIG. 7 shows process details for Boom flower-n 10% & 15% Granules formulation with Silica Quarts and granules.
Figure 8:
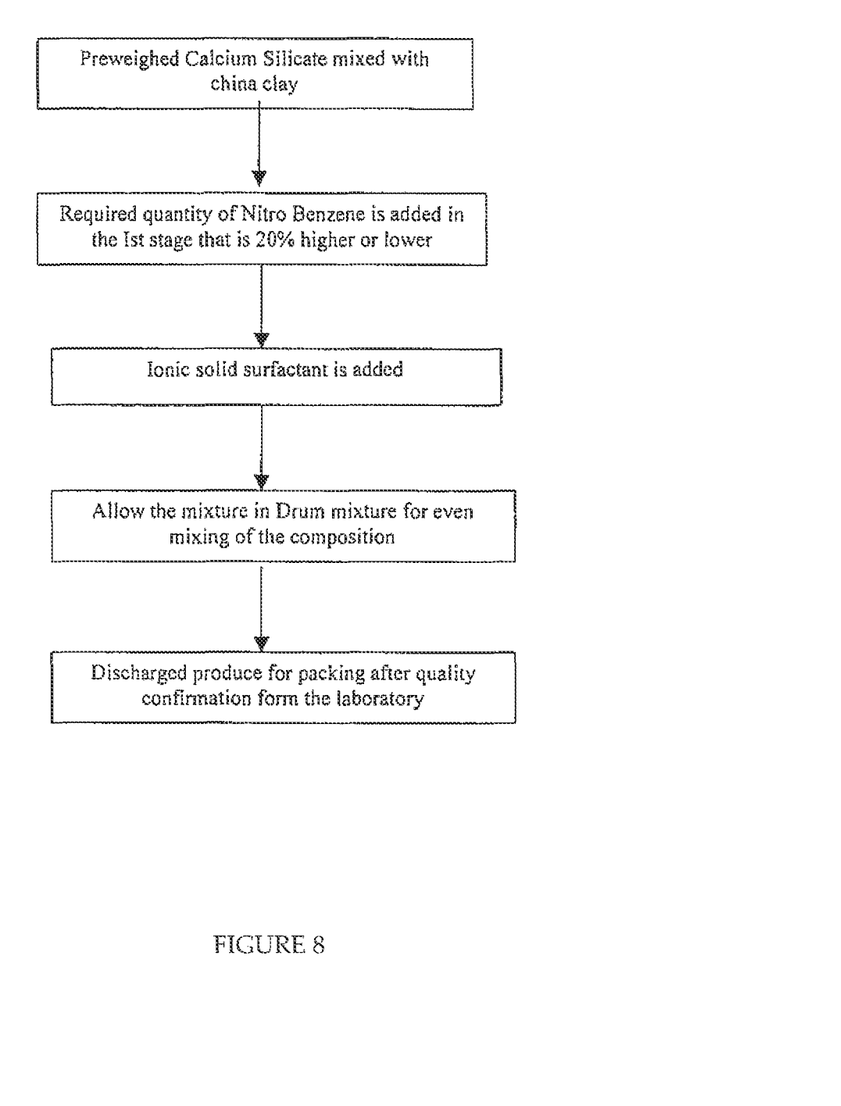
FIG. 8 shows process details for Boom flower-n 20% V/V wettable Powder formulation.

The novel composition will be made from the following raw materials:
Acid Slurry
Sodium Hydroxide
Bleaching material i.e. Urea
Aromatic Nitro compound i.e. Nitrobenzene—Active Ingredient The research team of the applicant, after years experience, searched, investigated and invented a product based on Aromatic Nitro compound i.e. Nitrobenzene which induces flowering in almost all flowering crops.

It is a unique product and there is no other product based on this chemical and processed in the unique way described herein. The Applicant's extensive field trials establish its use in an unequivocal manner. The exact formulation of each ingredient is investigated and made available in this complete specification.

The manner of manufacturing the said composition is given in the following description. The description refers to various flow chart which accompany this description. The process details are clearly described in each of the flow chart.

Acid Slurry of 8 to 10 kgs. is neutralized with Sodium Hydroxide. After neutralization it is bleached with 1 to 2 kgs of urea, producing 80 to 160 liters of liquid surfactant (IONIC Surfactant) which is cured sufficiently to stop froth etc. and used as a carrier.

Aromatic nitro compound i.e. 20 kgs. of Nitrobenzene is added to every 80 liters of liquid surfactant carrier and allowed to get absorbed in the liquid detergent by repeated stirring.

Devices used in the manufacturing process of flowering stimulant are given below:

Mixing vessel, agitator, filling machine, shrink packaging machine are required and according to output condition, automation is also required. The product can be utilized profitably in all flowering plants, trees, crops etc., It has been found that this flowering stimulant formulation when applied to all flowering plants gives excellent yield. No side effects were visible when using this flowering stimulant composition. It is to be noted that this flowering stimulant composition will have wide application.

Reference is invited to various flow charts which accompanying the description. Method or process details for obtaining various formulations is illustrated in each flow diagram.

EXAMPLE

The invention is further explained with the help the following examples which are intended to describe the salient features and to give a more detailed understanding of the invention. The particular amount, proportions, compositions and other particulars are meant to be exemplary and not intended to specifically limit the scope of invention.

Example No. 1

Acid slurry (Linear Alkyl Benzene) is added slowly to the measured quantities of Sodium Hydroxide (Caustic soda) in a high density plastic vessel (or) stainless steel container to secure a neutral solution strictly with pH 7.0. When the resultant product cools to room temperature, urea is added till a Honey colour is obtained. The resultant solution is then primed to required quantity i.e. volume by adding water.

Nitrobenzene is then slowly added and simultaneously stirred till uniform product with Aromatic smell is secured. (For optimal results the resultant flowering stimulant should contain 20% NITROBENZENE v/v and the formulation should have absorbed the active ingredient uniformly and should be in free flowing formulation easily mixable with water.

Example No. 2

In certain special cases and in certain sensitive crops, ionic surfactant base as described in above paragraph is not useful or is redundant.

In such cases, a non-ionic (totally organic or plant derived) surfactants (example—Glycol Ether) taken to predetermined level and N.B. (NITROBENZENE) is charged into the Non ionic medium till a 20% or a required concentration of flowering stimulant is obtained. Now a sophisticated Flowering stimulant cum quality improver, product "Boom Flower-n" is ready. (This will be a de-odorized, free flowing Fool-proof product and will easily have 3 to 4 years shelf life and is compatible with all Agro chemicals.

Example No. 3

To a measured quantity of Aromatic solvent (Say Aromax, CIX etc.), required quantity of Nitrobenzene and q.s. (quantum sufficientum) non ionic/Ionic/cationic emulsifier or mixed emulsifier) is added and thoroughly mixed in stainless steel formulation kettle to obtain the end product flowering stimulant and quality enriching Boom Flower in the form of a homogeneous mixture. It is compatible with all Agro Chemical.

Example No. 4

To a measured quantity of Roasted Bentonite clay, or unroasted Bentonite clay or silica quarts sand granules with calcium silicate absorbent, required quantity of Nitrobenzene with suitable coating agent is added and thoroughly mixed to obtain Nitrobenzene granules at 10% or 15% strength.

Example No. 6

To a measured quantity of a premixed mixture of calcium silicate as absorbent and China clay as a bulk carrier with ionic solid surfactant like carbaxyl methyl cellulose, required quantity of Nitrobenzene is added and thoroughly mixed to obtain the optimum composition possessing Nitrobenzene concentration of 20% higher or lower.

The following table illustrates the result of application of the product. It is evident from the illustration that the invention finds extensive application in agriculture and horticulture crops. The results of the application have been very encouraging and immensely beneficial to agricultural and horticultural crops.

Application

| Sl. No. | Name of Product | Name of Crop | Yield & increase | Quality improvement | Any other interesting Feature |
|---|---|---|---|---|---|
| 1. | Boom Flower'n' | Tomato | 30% to 40% | 34% to 40% Muttony Fleshy fruit with more Brix content | Improves Plant Growth |
| 2. | Boom Flower'n' | Brinjal (Egg-Plant) | 25% to 28% | 18% to 21% Flesh increase | Improves Plant Growth |
| 3. | Boom Flower'n' | Jasmine | 40% to 45% | PEDICIL Length increased | Size of Flower increase |
| 4. | Flower'n' Flower'n' | Cotton | 3% to 40% | | |
| 5. | Boom Flower'n' | Mango | 30% to 40% | Colour enriched | Uniform ripening |
| 6. | Boom Flower'n' | Rice | 20% to 25% | Uniform panicle emergence | 7–8 days advancement in flowering |
| 7. | Flower 'n' Flower'n' | Chillies | 30% to 35% | Size increase | Improves Plant Growth |
| 8 | Boom Flower'n' | Cardomom | 30% to 35% | Boldness | Improves Green Colour |

For all flowering crops, Boomflower-n granules can be used where spraying is not possible.

Detailed/Biochemical/Chemical trials are being carried out at the following institutions:

| a. | Chillies | Acharya Renga University of Agriculture Andhra Pradesh, India |
| b. | Redgram Crop (Pegeon Pea) | University of Agrl. Sciences, Dharwad - Karnataka. India |
| c. | Cotton | Punjab Rao Deshmukh Agricultural University at AKOLA, Maharashtra, India. |
| d. | Jasmine | M.Sc Student Fellowship at Tamil Nadu Agril. University, Coimbatore, India. |
| f. | Cardamom | Central Cardamom research station at Mayiladumparai, Idikki Dt, Kerala, India. |
| g. | Soya Bean | Punjab Rao Deshmukh Agricultural University, Akola, Maharastra, India. |
| h. | Rice | Tamilnadu Agriculture University, Aduthurai, Tamil Nadu, India. |
| i. | Wheat | Mahathma Pule Agricultural University at Rahuri Maharastra, India. |

I claim:

1. A flowering stimulant composition for agricultural or horticultural crops, wherein the composition comprises 20-22% by weight nitrobenzene in a liquid carrier, wherein the liquid carrier comprises a solvent base selected from the group consisting of: (a) an ionic surfactant base comprising urea and a neutralized product of an acid slurry comprising linear alkyl benzene with sodium hydroxide; and (b) a non-ionic surfactant base comprising a glycol ether.

2. The composition of claim 1, wherein the composition further comprises one or more fillers, and wherein the liquid carrier comprises an ionic surfactant base comprising urea and a neutralized product obtained from reacting an acid slurry comprising linear alkyl benzene with sodium hydroxide.

3. The composition of claim 1, wherein the composition further comprises one or more fillers, and wherein the liquid carrier comprises a nonionic surfactant base comprising a glycol ether.

4. The composition of claim 1, wherein the composition further comprises one or more fillers, one or more stabilizers, or combinations thereof.

5. A flowering stimulant composition as claim in claim 1, comprising the following ingredients per 100 kg of the composition:
   8 kg to 10 kg of an acid slurry comprising linear alkyl benzene;
   1 kg to 2 kg of sodium hydroxide;
   2 kg to 4 kg of urea;
   20 kg of nitrobenzene; and
   filler and stabilizer;
   wherein the proportion of the acid slurry and sodium hydroxide is selected to provide a neutral pH.

6. A flowering stimulant composition as claimed in claim 1, comprising the following ingredients per 100 kg of the composition:
   60 kg to 70 kg glycol ether;
   20 kg nitrobenzene; and
   filler and stabilizer.

7. A method of stimulating flowering in agricultural or horticultural crops, the method comprising applying the flowering stimulant composition of claim 1 to an agricultural or horticultural crop.

8. A method of manufacturing the flowering stimulant composition of claim 1, the method comprising: neutralizing, using sodium hydroxide, an acid slurry comprising linear alkyl benzene to provide an ionic surfactant base; adding urea to the ionic surfactant base; and adding nitrobenzene to the ionic surfactant base so that nitrobenzene is present in the ionic surfactant base at 20-22% by weight.

9. The composition of claim 1, wherein the liquid carrier comprises an ionic surfactant base comprising urea and a neutralized product of an acid slurry comprising linear alkyl benzene with sodium hydroxide.

* * * * *